United States Patent
Findlay et al.

(10) Patent No.: US 10,438,473 B2
(45) Date of Patent: Oct. 8, 2019

(54) ACTIVITY MONITOR

(71) Applicant: BUDDI LIMITED, Rickmansworth, Hertfordshire (GB)

(72) Inventors: Ewan Findlay, Milnathort (GB); Sara Murray, Rickmansworth (GB)

(73) Assignee: Buddi Limited, Rickmansworth, Hertfordshire (GB)

(*) Notice: Subject to any disclaimer, the term of this patent is extended or adjusted under 35 U.S.C. 154(b) by 0 days.

(21) Appl. No.: 15/555,062

(22) PCT Filed: Mar. 7, 2016

(86) PCT No.: PCT/GB2016/050601
§ 371 (c)(1),
(2) Date: Aug. 31, 2017

(87) PCT Pub. No.: WO2016/142672
PCT Pub. Date: Sep. 15, 2016

(65) Prior Publication Data
US 2018/0040222 A1    Feb. 8, 2018

(30) Foreign Application Priority Data
Mar. 9, 2015    (GB) ................................. 1503914.2

(51) Int. Cl.
*G08B 21/04*    (2006.01)
*G10L 99/00*    (2013.01)
*A61B 5/00*    (2006.01)
*A61B 5/0205*    (2006.01)
*A61B 5/11*    (2006.01)

(52) U.S. Cl.
CPC ...... *G08B 21/0423* (2013.01); *G08B 21/0469* (2013.01); *G10L 99/00* (2013.01); *A61B 5/0017* (2013.01); *A61B 5/0095* (2013.01); *A61B 5/0205* (2013.01); *A61B 5/1118* (2013.01); *A61B 5/6802* (2013.01)

(58) Field of Classification Search
CPC ................ G08B 21/02; G08B 21/0202; G08B 21/04–0492; G08B 25/016; G08B 21/0423; G08B 21/0469; G10L 99/00; A61B 5/0017; A61B 5/0095; A61B 5/0205; A61B 5/1118; A61B 5/68
USPC .................. 340/573.1, 573.4, 539.11–539.15
See application file for complete search history.

(56) References Cited

U.S. PATENT DOCUMENTS

| | | | | |
|---|---|---|---|---|
| 5,499,196 A | * | 3/1996 | Pacheco ................. | G08B 25/14 702/81 |
| 6,611,206 B2 | * | 8/2003 | Eshelman .......... | G08B 21/0423 340/573.1 |
| 7,145,462 B2 | * | 12/2006 | Dewing ............. | G08B 21/0423 340/573.1 |

(Continued)

FOREIGN PATENT DOCUMENTS

| | | |
|---|---|---|
| GB | 2 505 985 A | 3/2014 |
| JP | H08124063 A | 5/1996 |

(Continued)

*Primary Examiner* — Nay Tun
(74) *Attorney, Agent, or Firm* — Haynes and Boone LLP

(57) ABSTRACT

An activity monitor comprising one or more acoustic transducers (100) and a computation component (104) that is arranged to identify events from acoustic signals received by the acoustic transducers (100).

18 Claims, 7 Drawing Sheets

(56) References Cited

U.S. PATENT DOCUMENTS

| | | | | |
|---|---|---|---|---|
| 8,830,059 | B2* | 9/2014 | Nikolovski | G08B 21/02 340/539.11 |
| 9,349,372 | B2* | 5/2016 | Fusakawa | G10L 25/51 |
| 9,373,246 | B2* | 6/2016 | Fiske | G08B 5/36 |
| 9,495,350 | B2* | 11/2016 | John | G06F 17/27 |
| 9,843,621 | B2* | 12/2017 | Thapar | G06Q 10/109 |
| 2003/0086341 | A1* | 5/2003 | Wells | G06F 17/30017 369/13.56 |
| 2006/0017561 | A1 | 1/2006 | Albert | |
| 2006/0196953 | A1* | 9/2006 | Simon | G05D 23/1934 236/46 R |
| 2007/0183604 | A1* | 8/2007 | Araki | G10L 17/26 381/58 |
| 2008/0025477 | A1 | 1/2008 | Farhan | |
| 2009/0085873 | A1 | 4/2009 | Betts et al. | |
| 2009/0115635 | A1* | 5/2009 | Berger | G01H 3/08 340/943 |
| 2010/0008515 | A1* | 1/2010 | Fulton | H04R 3/005 381/92 |
| 2013/0268273 | A1 | 10/2013 | Chen et al. | |
| 2014/0278388 | A1 | 9/2014 | Watson et al. | |
| 2014/0278412 | A1 | 9/2014 | Scheffer et al. | |
| 2015/0145993 | A1* | 5/2015 | Scalisi | G08B 25/10 348/143 |

FOREIGN PATENT DOCUMENTS

| | | |
|---|---|---|
| JP | 2007179491 A | 7/2007 |
| JP | 2011237865 A | 11/2011 |
| WO | WO 02/075688 A2 | 9/2002 |
| WO | WO 2004/062496 A1 | 7/2004 |
| WO | WO 2009/153681 A | 12/2009 |
| WO | WO 2011/045500 A1 | 4/2011 |
| WO | WO 2012/119253 A1 | 9/2012 |
| WO | WO 2014/022659 A1 | 2/2014 |
| WO | WO 2015/004909 A1 | 1/2015 |

* cited by examiner

ACTIVITY MONITOR

CROSS-REFERENCE TO RELATED APPLICATIONS

This application is a U.S. national stage continuation application under 35 U.S.C. § 371 of International Patent Application No. PCT/GB2016/050601 filed on Mar. 7, 2016, which claims the benefit of Great Britain Patent Application No. 1503914.2 filed on Mar. 9, 2015, the contents of each of which are incorporated herein by reference.

TECHNICAL FIELD

The present disclosure relates to an activity monitor, and in particular for an activity monitor that detects activities of one or more persons and/or animals, usually in a home or other building.

BACKGROUND

Various personal monitors have been proposed to assist in the care of elderly, infirm or vulnerable people, or the supervision of other individuals. These personal monitors include devices with equipment such as accelerometers designed to detect when someone falls, panic buttons which can be pressed when an individual gets into trouble, and tracking devices that can be used to detect when an individual wanders outside of a specific area. These tracking devices may be intended to allow those with memory loss, frailty, or symptoms of dementia to live more independent lives in their own homes rather than in care-homes.

All of these personal monitors must be carried by the person being monitored (the user) in order to be effective. The requirement to wear a device is inconvenient for the person being monitored, and introduces a source of error if the user does not carry or wear the device, either through forgetfulness, discomfort, inconvenience or a deliberate attempt to avoid being monitored.

Whilst detecting or generating alerts for singular events such as falls or other emergencies is highlighted as a priority, there is also a need for an activity monitor that can measure other activities or behaviours, and also to derive trends from these monitored activities.

To illustrate this we consider the example area of caring for elderly or infirm people. A major problem affecting the quality of life of elderly or infirm people is loneliness. Any attempts to address loneliness amongst the elderly have been centred on services such as care-worker visit time and telephone contact lines. However these approaches do not address the root causes of loneliness. The former can be overly targeted on the elderly person's physical needs and may be perfunctory in nature given the limited time that is allotted to each visit. The latter requires the elderly person to realise that they are lonely and feeling down and then act to remedy it.

In all cases there is no attempt to measure loneliness. There is a correlation between the amount of interpersonal contact one has and how lonely one feels. Although different people need different amounts of contact to feel connected, being able to relate an amount of interpersonal contact to their level of well-being would give a potential trigger for intervention such as extended care-worker visits. Someone whose neighbours visit twice daily would be expected to have a different degree of loneliness from someone who only has two twenty minute care worker visits or no visitors at all.

Again considering the example of elderly or infirm people, there are also scenarios where a person can get into difficulties and a fall detector or panic alarm does not detect that an emergency has occurred, either because the device is not being worn or the nature of the event cannot be detected by the device. A monitor system that detects other types of activities could be used to intelligently infer that the person is in an emergency situation.

Accordingly, there is a need for an activity monitor that can detect activities or behaviours of a monitored person or animal. It would also be desirable for an activity monitor to identify trends from identified activities. It would also be desirable to implement an activity monitor without requiring a wearable device.

SUMMARY OF THE DISCLOSURE

According to a first aspect of the disclosure there is provided an activity monitor comprising one or more acoustic transducers and a computation component that is arranged to identify events from acoustic signals received by the acoustic transducers.

Optionally, the identification of events is based on acoustic signals of relatively low frequency, whereby intelligible speech is not captured.

Optionally, the activity monitor comprises an electronic filter circuit coupled with the acoustic transducer that filters out frequency components of the acoustic signal which relate to intelligible speech.

Optionally, the identification of events is based on infrasound acoustic signals.

Optionally, the computation component comprises:
means for sampling a time slice of an incoming acoustic signal;
means for deriving an acoustic amplitude vector from the sampled time slice;
a frequency transform means that generates a frequency domain representation of the time slice;
means to combine the acoustic signal and the frequency domain representation of the time slice to form an acoustic vector; and
a statistical model based pattern recognition component arranged to analyse the acoustic vector for identification of an event.

Optionally, the computation component comprises means to transform the acoustic vector into a parameter space comprising axes which correspond to characteristics of interest.

Optionally, the computation component comprises a local data store comprising a library of pre-stored or learned events.

Optionally, the computation component is arranged such that, if an acoustic vector is not matched to an event by the local data store, the computation component sends the acoustic vector to a server which comprises a library of events and which compares the acoustic vector with the library; and if a match is found, the server sends information back to the computation component which then updates its local data store.

Optionally, the computation component comprises an event classifier that identifies actions formed from sequences of events.

Optionally, a likelihood of an action being performed is derived from a combination of a linear progression of events in a prescribed order; and the presence of supplementary events in any order.

Optionally, the computation component comprises an activity classifier that identifies activities formed from sequences of actions.

Optionally, the computation component comprises an inference engine that infers a routine from identified actions or activities.

Optionally, the computation component comprises an inference engine that infers a social interaction from identified actions or activities.

Optionally, the computation component comprises an inference engine that infers a sudden break in routine from identified actions or activities, to indicate a possible traumatic event.

Optionally, the activity monitor comprises means for monitoring movement of a person.

Any suitable means can be provided, including infra-red, microwave or ultrasonic sensors.

Optionally, the activity monitor can identify movement in specific rooms and/or use of specific doors within a building.

Optionally, the activity monitor can learn the voice of a user and identify additional voices.

Optionally, the activity monitor can measure the duration of visit, by recording time periods of different voices, the time between doors being opened or closed, or other parameters.

Optionally, the activity monitor can measure the proportion of conversation spoken by each participant in the conversation.

Optionally, the activity monitor can monitor level of animation, tone of voice, and other parameters.

Optionally, the activity monitor can store voices and identify regular visitors and monitor timing and duration of their visits.

Optionally, the activity monitor can rank voices on male-female scale, giving scores to voices.

Optionally, the activity monitor can rank voices on age-related scale, giving scores to voices.

Optionally, the activity monitor comprises a plurality of acoustic monitoring units.

Optionally, acoustic monitoring units are provided in a plurality of rooms or areas of a building, or a plurality of areas of an outdoor space.

Optionally, each of the acoustic monitoring units comprises an acoustic transmitter and are arranged such that outputs of one or more acoustic transmitters can be used to determine relative positions between two or more acoustic monitoring units and so to triangulate the position of a detected sound.

According to a second aspect of the disclosure there is provided a method of monitoring activity, comprising obtaining acoustic signals and computationally identifying events from the acoustic signals.

According to a third aspect of the disclosure there is provided a computer program product comprising instructions that, when executed by a computer, enable it to act as the computation component of the first aspect.

The computer program product may be stored on or transmitted as one or more instructions or code on a computer-readable medium. Computer-readable media includes both computer storage media and communication media including any medium that facilitates transfer of a computer program from one place to another. A storage media may be any available media that can be accessed by a computer. By way of example such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fibre optic cable, twisted pair, digital subscriber line (DSL), or wireless technologies such as infra-red, radio, and microwave, then the coaxial cable, fibre optic cable, twisted pair, DSL, or wireless technologies such as infra-red, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, where discs reproduce data optically with lasers. Combinations of the above should also be included within the scope of computer-readable media. The instructions or code associated with a computer-readable medium of the computer program product may be executed by a computer, e.g., by one or more processors, such as one or more digital signal processors (DSPs), general purpose microprocessors, ASICs, FPGAs, or other equivalent integrated or discrete logic circuitry.

BRIEF DESCRIPTION OF THE DRAWINGS

The disclosure will be described below, by way of example only, with reference to the accompanying drawings, in which.

DETAILED DESCRIPTION

The present disclosure provides various solutions the automatic monitoring of activities of people or animals, usually within buildings (outdoor use is not excluded from the scope of the disclosure).

One example area of application is the automatic monitoring of the well-being of the elderly and infirm. The disclosure may have utility in one or more aspects of well-being including loneliness, which can be monitored to some degree by the level of interpersonal interaction; liveliness, which may be monitored in terms of levels of activity; and the stability of a daily routine, which can be measured as a pattern regularity, indicating healthy patterns of activity including as non-limiting examples sleeping well and getting up to make and eat breakfast.

Currently there is no device capable of monitoring these facets of life and drawing useful conclusions about both long-term trends in well-being and individual detrimental events. The solution of the present disclosure is based on acoustic signature monitoring.

Appropriate intelligence may be provided (via filtering circuits and algorithms) to distinguish the sounds made by the user in their home from those generated by artificial sound sources such as televisions, radios and other machines for relaying live and recorded sounds; those originating outside the dwelling from natural and artificial sources; and those generated by neighbours. Additionally the privacy of the user will be preserved in a technically transparent fashion, which can be demonstrated to the user, their relatives and caregivers.

Figure 1:
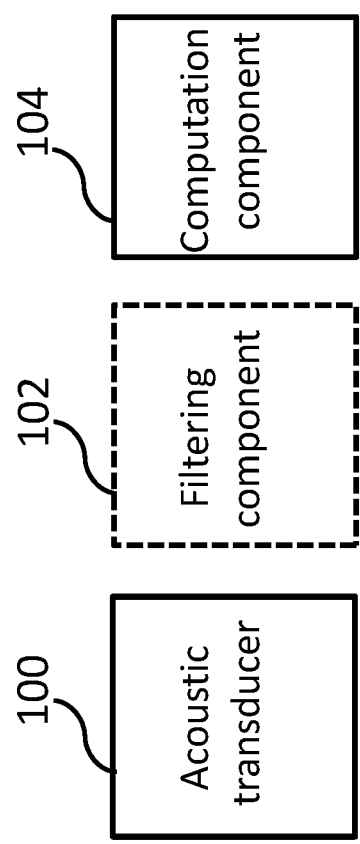
FIG. 1 shows general principles of an activity monitor according to an embodiment of the disclosure.

There are various ways in which an activity monitoring system according to the disclosure can be implemented. Basic components of the system are illustrated in FIG. 1. The system comprises an acoustic transducer 100 such as a microphone, and a computation component 104. The computation component 104 is capable of interpreting the incoming acoustic signals gathered by the acoustic transducer 100 and assigning a cause to them, preferably using a combination of filtering and statistically-based identification models. An optional filtering component 102 may also be provided, which filters the received acoustic signals as will be discussed in more detail below.

An acoustic monitoring unit comprises a housing that contains at least an acoustic transducer. According to an embodiment of an activity monitor system, an activity monitoring system comprises a single acoustic monitoring unit which includes both the acoustic transducer 100 and computation component 104. The device also comprises a digital memory and an interface so that a log of data derived by the computation component 104 can be accessed. The interface would preferably comprise a communications link for sending the data to a remote server, but that is not essential. It is possible for the user or a visitor to manually access the interface to access the data that has been gathered. The device may suitably include a USB or other similar interface and present itself to a computer (or other suitable device) as a mass storage device for transfer of log files, or alternatively a wireless interface for sending the data through atmospheric space. These log files could be copied and interrogated with a suitable application running on a computer that connects to the device.

In other embodiments, a plurality of acoustic monitoring units are provided. They may be provided in a plurality of rooms or areas of a building or outdoor space, and there may be a plurality in one or more of each room or area.

Figure 2:
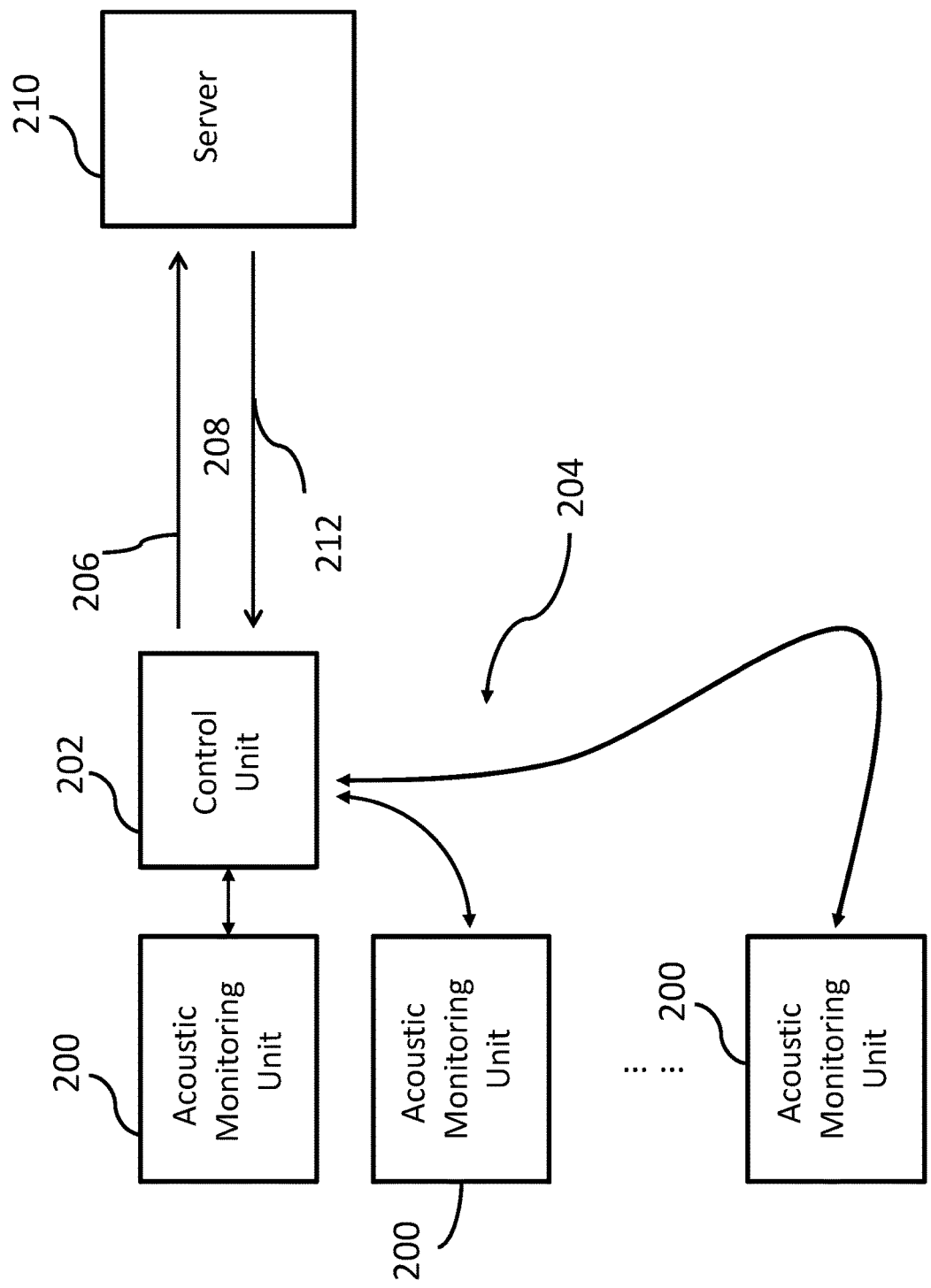
FIG. 2 shows an embodiment of an activity monitor system with a plurality of acoustic monitoring units, a control unit and a remote server.

The computational component 104 may be provided in a dedicated control unit which may be coupled with one or more acoustic monitoring units. FIG. 2 shows an example of how various components of an activity monitoring system according to an embodiment may be arranged. Here the activity monitoring system comprises a plurality of acoustic monitoring units 200 (the dotted lines indicate that there may be further units), each of which contains an acoustic transducer 100. The acoustic monitoring units 200 also contain an interface for communicating with a control unit 202. The communication links 204 between the monitoring units 200 and the control unit 202 may be wired connections such as Ethernet, data over mains technology or any other suitable means, or wireless connections whereby a signal is transmitted through atmospheric space such Wi-Fi, Bluetooth or any other suitable means, including those related to optical free-space transmission.

The control unit 202 sends acoustic data 206 for identification over a communications link 208 to a server 210 which may be located remotely from the other components. The communications link 208 may comprise a telephone network, including a landline network, local area computer networks and the networks provided by mobile communications (e.g., GSM, etc.). The control unit 202 may pre-process and compress the acoustic information appropriately before transmission to the server 210. The server 210 processes the data. It may identify an event, action or activity and provide an alert signal or status report information to appropriate third parties. It may also optionally send back a derived or identified acoustic signature 212 to the control unit 202, which can be stored locally at the control unit 202 to enhance its capabilities. For example, the control unit could locally store a set of operations which identify the type of sound, with its capability limited by a set of signature-type-identifiers held locally in memory. When a new type of sound is heard it is labelled 'unidentified' and sent to the server where it is identified and the resulting signature-type-identifier is returned to the control unit to be used in future classifications.

Therefore in this embodiment the system's computational component 104 is effectively distributed between the control unit 202 and the server 210, with the choice of tasks to be carried out by each of the control unit 202 and the server 210 chosen to optimise computation times and volume of data being sent over the network.

The control unit 202 can take various forms including: a hub device without an acoustic monitoring device capable of receiving signals from all acoustic monitoring devices; a home computer or other non-specific computational device (including mobile telephones, tablet computers, a smart tracker unit et cetera) capable of receiving signals from all acoustic monitoring devices; or a non-specific computational device fitted with a function-specific hub-receiver capable of receiving signals from all acoustic monitoring devices.

In other embodiments the computation component may reside entirely at a server. Alternatively, the computation component may reside entirely at a control unit, or entirely at an acoustic monitoring unit. Where a plurality of acoustic monitoring units are provided, one of them may also comprise part of the whole of the computation component.

In alternative embodiments, the computation component 104 may be distributed between one or more of the acoustic monitoring units and other components comprising a control unit and/or a server. Any portion of the relevant computation tasks can be distributed amongst a plurality of acoustic monitoring devices if the system is configured appropriately.

The interpretations of the acoustic signals can be used to assess the user's well-being, both in the short term and the long term. An instance of a short-term use would be recognising that a sequence of events related to getting up in the night and returning to bed was not completed within a given time frame; thus indicating the potential collapse of the user. An instance of a long-term use would be monitoring the interpersonal interaction levels over a week and assessing the potential for an increased level of loneliness from week to week.

In cases where a plurality of acoustic monitoring units are distributed, their function can be improved by triangulation to ascertain the position of the sound source. To facilitate this each of the separate acoustic monitoring units can output coordinated, identifiable sounds from which the time of travel to the other units can be measured. Preferably this is done sequentially, allowing the same sound to be produced by each unit. Ideally the units are positioned around the perimeter of the volume of interest (such as a user's home).

Figure 3:
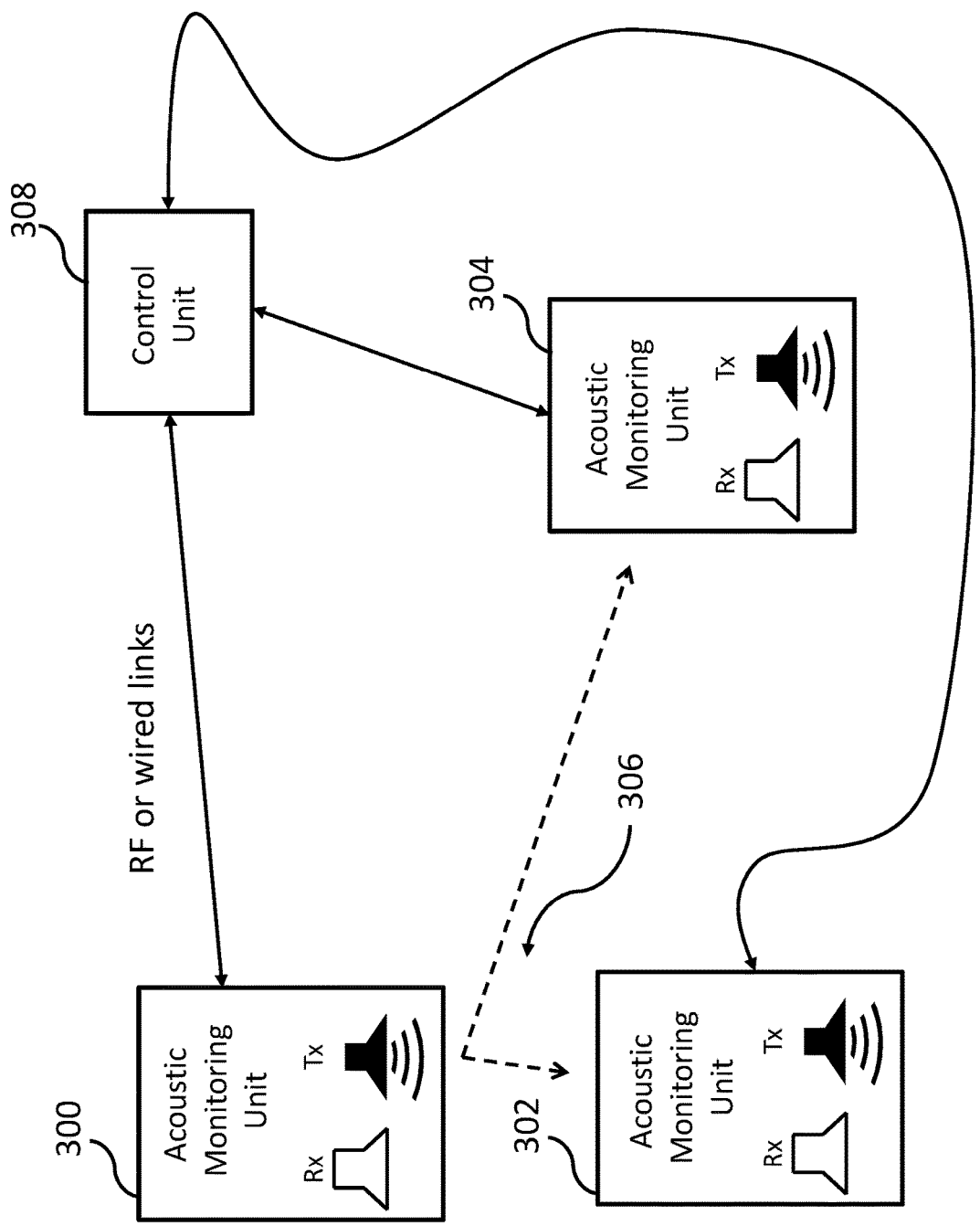
FIG. 3 shows the triangulation of relative positions of three acoustic monitoring units by transmission of known sound patterns.

FIG. 3 shows a control unit 308, and three acoustic monitoring units 300, 302, 304. Each acoustic monitoring unit is equipped with an acoustic transmitter (Tx) in addition to its receiver (Rx). One unit (300) emits an acoustic identification signal 306. In this case the acoustic travel time the emitting unit 300 to each of the other units 302 and 304 can be calculated. Ideally if the exact positions of four or more appropriately distributed units with respect to each other are known then the position of a sound source in a volume can be identified. Note that only three units would be required to assess position in a single story dwelling. In the case where we know that the units are on the perimeter of the user's home we can easily identify that a sound originates within its volume. When the units are not on the perimeter of the home other clues can be used to estimate the travel time to the external walls such as the arrival of echoes and other reverberations of the acoustic identification signal as received at the different acoustic monitoring units and as well as those received back at the emitting unit 300.

Figure 4:
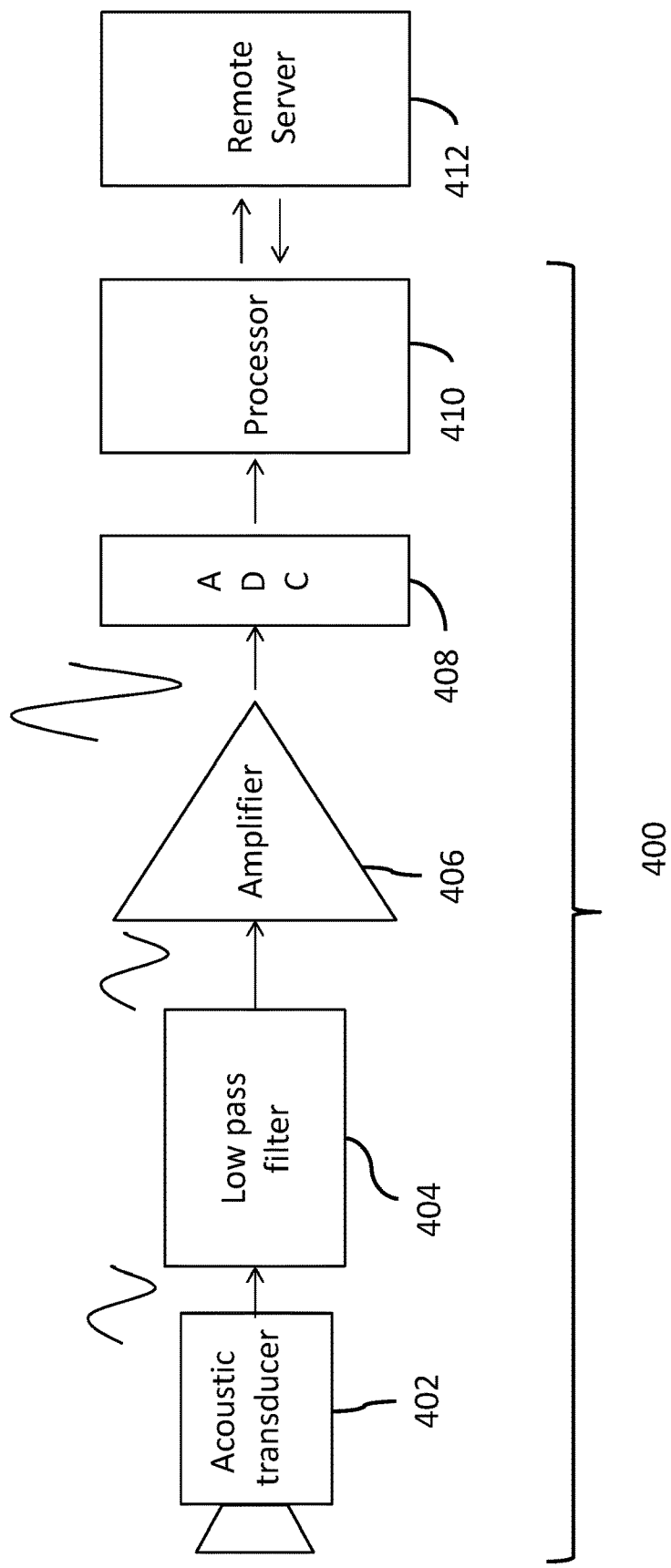
FIG. 4 shows a block diagram of acoustic detection and processing circuitry which may be provided as part of an acoustic monitoring unit.

FIG. 4 shows an example embodiment of an acoustic monitoring unit 400 that can be used with the arrangements shown in FIGS. 1-3 and in various other embodiments. The unit comprises an acoustic transducer 402 such as a MEMS microphone, an electronic low pass filter circuit 404, an amplifier 406, an analogue to digital converter 408, and a processor 410. The processor is in communication with a remote server 412.

The acoustic transducer 402 is preferably a microphone with a response allowing reception of very low acoustic frequencies, ideally including infra-sound frequencies and preferably including those below 10 Hz. It may be decoupled to the rest of the electronic circuit, with a resulting response below 1 Hz which extends to above 1 kHz in a predictable manner. Ideally the response between 1 Hz and 2 kHz is linear with sound pressure, with a deviation of less than 5% from the average responsivity. Ideally the microphone response shall not drop by more than 50% of its 10 Hz to 2 kHz level at frequencies>5 Hz. It is appreciated that these performance characteristics are provided for illustration only and that the scope of the disclosure is not limited to the use of transducers/microphones with these particular characteristics.

The electronic low pass filter circuit 404 will be devised such as to remove all signals above the Nyquist frequency that the signal will be sampled at, thus minimising the effects of spurious noise. The electronic low pass filter circuit 404 may have an upper cut-off frequency devised such as to make speech unintelligible when directly relayed without digital processing. This is designed to ensure that actual speech is not recorded, to safeguard a user's privacy. The fact that the cut-off frequency is defined in hardware means that this privacy feature is demonstrable to third parties and cannot be "switched off" by the maker of the device. The analogue low pass filter circuit 404 will be directly followed by an analogue-to-digital conversion circuit 408.

On conversion to the digital domain the signal is analysed for two different types of acoustic information: infra-sound generated by mechanical events such as doors opening or footsteps; and time evolving frequency content found in both the acoustic signals generated by mechanical events and speech. The combination of the infra-sound information and the time evolving spectral information from an acoustic signature for an event. Patterns in these acoustic signatures can be analysed to infer a sequence of events that make up an action, and patterns within the inferred actions can be used to form a picture of daily routines and interpersonal interactions. Infra-sound is defined as sound with a frequency lower than around 20 Hz.

As an example, an action may comprise a sequence of events comprising a plurality of footsteps of a person walking across a carpeted suspended wood floor, then a plurality of footsteps of a person walking across a hard concrete floor and finally, opening a door. The infra-sound content of the footsteps will change on going from the wood floor to the concrete one, as will the spectral content of the associated resonances. The door opening event will generate a pressure impulse and there will also be characteristic clicks from the catch of the door. Each of these events can be identified individually: footstep-wood, . . . , footstep-wood, footstep-concrete, . . . , footstep-concrete, release door catch, door-open. Also, the sequence of the events infers the action "go to door"; optionally with the specific door being identified either through triangulation or through previous learning of its unique signature; and this action may be classified as such in the data stored or available to the appropriate agencies from the remote server. If there is no context (such as a door opening event) to be inferred, the action of walking can be labelled generally as "movement".

One activity that may follow opening a door is a visit. In this case voices and/or a second set of footsteps entering the home will be detected by the acoustic monitor(s). In the case of voices being heard, the durations of the conversation and visit, the portion of the conversation occupied by the user speaking and number of distinct voices heard may be stored or relayed to the server. Other aspects of the conversation can be monitored including the level of animation, the tone of voice and so forth. Such information can be used to infer the level and sort of interpersonal interaction.

The specific voice of the user can be identified by a learning algorithm. Ideally this would require no prescriptive learning procedure for the user; for example, the user's voice signature could be ascertained as being the most frequently heard amongst other voices over time. However, if necessary, the user's voice could be registered as part of the system's installation process. Also, other voices' signatures can be assessed for their distinctiveness and be scored for their similarity to previously heard voices. This allows regular visitors to be identified and the timing and duration of visits to be monitored. As the device is intentionally made deaf to the word content of the conversation, preferably in the analogue circuitry, such monitoring will not constitute a breach of privacy.

The identification of voices as with other sounds will be based on spectral content and its time evolution. When identifying voices from their lower frequency ranges, it is relatively straightforward to rank voices on a male-female scale, giving scores to voices as appropriate, which may be used as a basis for identifying specific speakers.

Scoring acoustic signatures for their various qualities can take a number of forms. An acoustic signal related to an event can be regarded as the combination of a low frequency temporal pattern related to impulses present in the infrasonic range and a time-evolving spectrum of its overall frequency content only limited by the analogue low pass filtering circuit. On digitisation, the acoustic signal is filtered with an extreme low pass filter (for example, 3 dB point of less than 40 Hz and preferably less than 20 Hz) to provide a pattern of time-evolving impulses related to events.

The digital low pass filter may take the form in the time domain of a sine cardinal function, Gaussian or other common digital filter form. The cut off frequency of the low pass filter is dictated by the length of the time slice. The cut off frequency can be chosen to be in the range $$f_{cut\ off} = \left[\frac{1}{2 \cdot t_{slice}}, \frac{1}{t_{slice}}\right]$$

to minimise duplication of analysis. The low frequency data can be analysed by measuring rise/fall times and observing general waveform shapes to identify events. Alternatively, the low frequency data can be binned and undergo a direct Fourier transform, or other transformation into the frequency space for low frequency event identification over longer timescales than that for the time slice. Alternatively, the averages over the time slices can be used as a means of generating a low frequency response.

Also, time slices of the digitised acoustic signal are sampled, using a Hamming window or similar to remove sampling edge effects, and a frequency spectrum is generated for that slice. Sampling theory dictates that the length of the time-slice is related to both the frequency resolution that can be achieved and the minimum frequency that can be detected by subsequent analysis.

There are a myriad of techniques that can be employed to analyse the spectral content of the time slice. As a basic initial step we need to extract the power spectrum of the signal. Phase and amplitude spectra could also be generated for the time slice. The power spectrum can be extracted using any suitable technique including using discrete Fourier transforms, discrete cosine transforms, linear prediction or a series of band-pass filters. At this point the spectral content can be subjected to a weighting function and/or a smoothing function. An example of a common weighting function is taking a logarithm to boost the relative content of higher frequencies, as is done in cepstrum generation. Another example would be simply multiplying the spectrum with a linear or polynomial function of frequency.

A subsequent transformation step may be employed where the weighted spectrum is converted back into the time domain.

Figure 5:
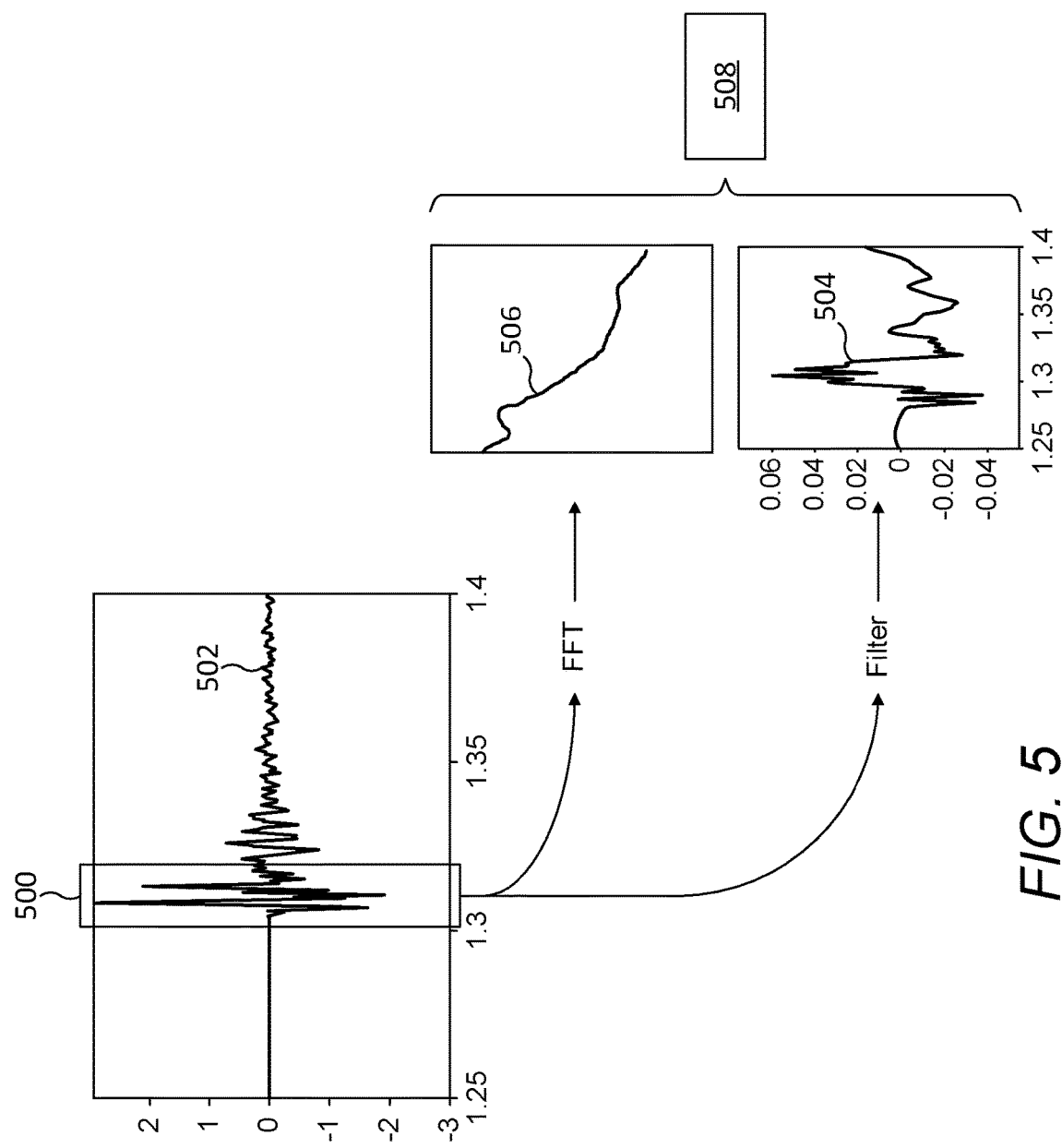
FIG. 5 shows the process of taking a temporal slice of a signal and applying filters and transforms to arrive at temporal and spectral characteristics of interest, which are combined to form a representative acoustic vector for the time-slice.

The weighted and smoothed output of each time-slice after spectral processing forms a vector which can either be complex, containing the relative phase information of the frequency content, or real, containing just the magnitude of each frequency component. In all cases the spectral vector evolves with time, as does the simple infra-sonic amplitude vector. The two vectors can be combined to give an acoustic characteristic vector. This is illustrated in FIG. 5, which shows the process of taking a temporal slice 500 of a signal 502 and applying a filter and a transform (FFT for example) to arrive at temporal characteristics 504 and spectral characteristics 506 of interest. The power spectrum for the time slice 500 and the low frequency amplitude vector evolution over the time slice 500 are then combined to form a representative raw acoustic vector 508 for the time slice 500 at time t (t being the chosen reference point for the time slice; e.g. the start time, mid-point or end of the time slice).

To aid in subsequent processing the acoustic characteristic vector 508 may be transformed into a parameter space showing a higher degree of separation for the characteristics of interest. An example would be a mapping to a two-dimensional space estimating age and male-femaleness. Markers of voice age and sex could be taken within the frequency domain and projected onto axes for those parameters. The actual physical origins of the markers include the size of the voice box and head as well as the elasticity of the vocal cords. The resultant multidimensional combination of frequency and modulation markers can be mapped onto a continuous two dimensional space estimating age and male-femaleness. Clearly this is not exact and should be regarded as a likelihood. Such a transformation can be derived prior to installation or by using an appropriately derived interactive statistical model such as a principle components analysis (PCA) or similar technique.

Figure 6:
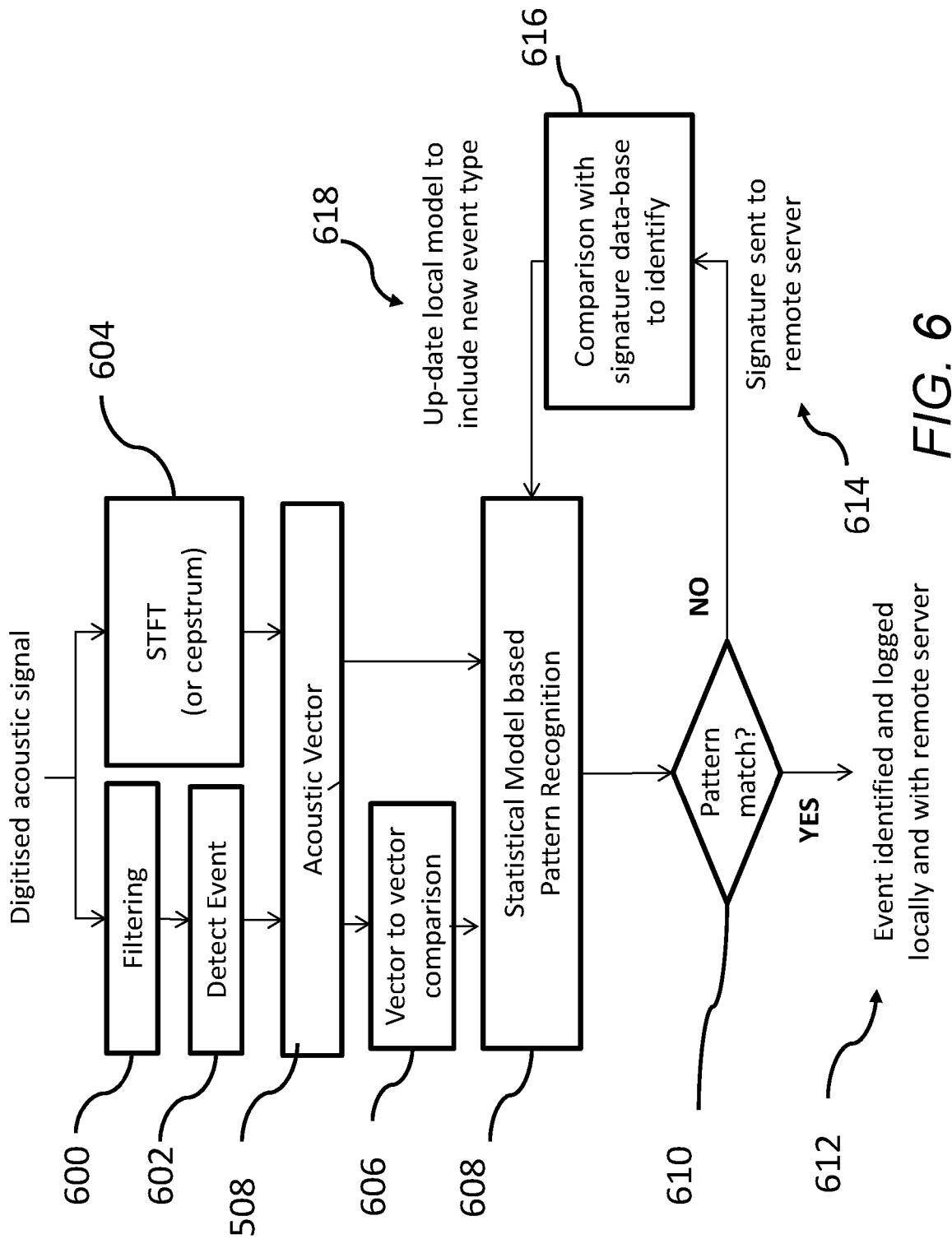
FIG. 6 shows the process of FIG. 5 in block diagram form to arrive at the acoustic vector which is then fed into a statistical pattern recognition algorithm a linked to a remote server.

To identify events and speakers patterns within the temporal evolution of the acoustic characteristic vector we may use a combination of comparison techniques internal to the set of evolving acoustic characteristic vectors mixed with machine learning techniques, as illustrated in FIG. 6. This shows the process of FIG. 5 in block diagram form, including infra-sound information (filtering 600 and event detection 602) and time-evolving frequency content (frequency conversion 604) which are combined to arrive at the acoustic vector 508. An optional vector-to-vector comparison 606 can be performed to smooth out noise or for other statistical purposes; and acoustic vector 508 and/or the outputs of the comparison 606 are input to a statistical pattern recognition module 608 which stores and applies an appropriate statistical pattern recognition algorithm.

The statistical pattern recognition module 608 may be provided as part of a control unit or as part of an acoustic monitoring unit. As there may be a limitation to the processing power and memory capacity locally to the acoustic monitoring device and/or its control unit, the acoustic signature comparison may be partly implemented using a server which may be remote from the control unit or acoustic monitoring unit. If the statistical pattern recognition module 608 identifies a match (at 610), the event is identified and logged, both locally and with the remote server. If a match is not identified (at 610), the captured signature may be sent to the remote server (614), which makes a comparison 616 with its own signature database to identify the event. In the event that an event is identified, the server sends back a new event type (618) which updates the statistical pattern recognition module 608, installing it in the local memory.

Comparison techniques can extract characteristics such as the nature of modulation at different frequencies in the spectra. Statistical techniques as applied to the evolution of acoustic vectors are used to perform functions such as acoustic signal type identification and generation of new signatures within known types. A good example of both comes from the voice signatures where the algorithm identifies the signal as conforming to the general type 'voice,' parameterising it and giving it a likelihood score, then builds a specific acoustic signature labelling it as voice "X", distinct from other voices. Given the nature of the system and function of the present disclosure, the most applicable techniques are seen as Vector Quantisation or Gaussian Mixture Models, artificial neural networks and Support Vector Machines and other sparse kernel machines including Relevance Vector Machines, although it will be appreciated that other techniques may be used.

On having identified a series of events using the statistically derived event model, the system then has to identify a series of events that forms an action. This may also be achieved using a heuristic algorithm that can either be constructed using standard computational techniques, or based on statistical machine learning techniques. The heuristic algorithms use the identified events to build identified actions and therefore routines as well as identifying various aspects of conversation (FIG. 7).

Figure 7:
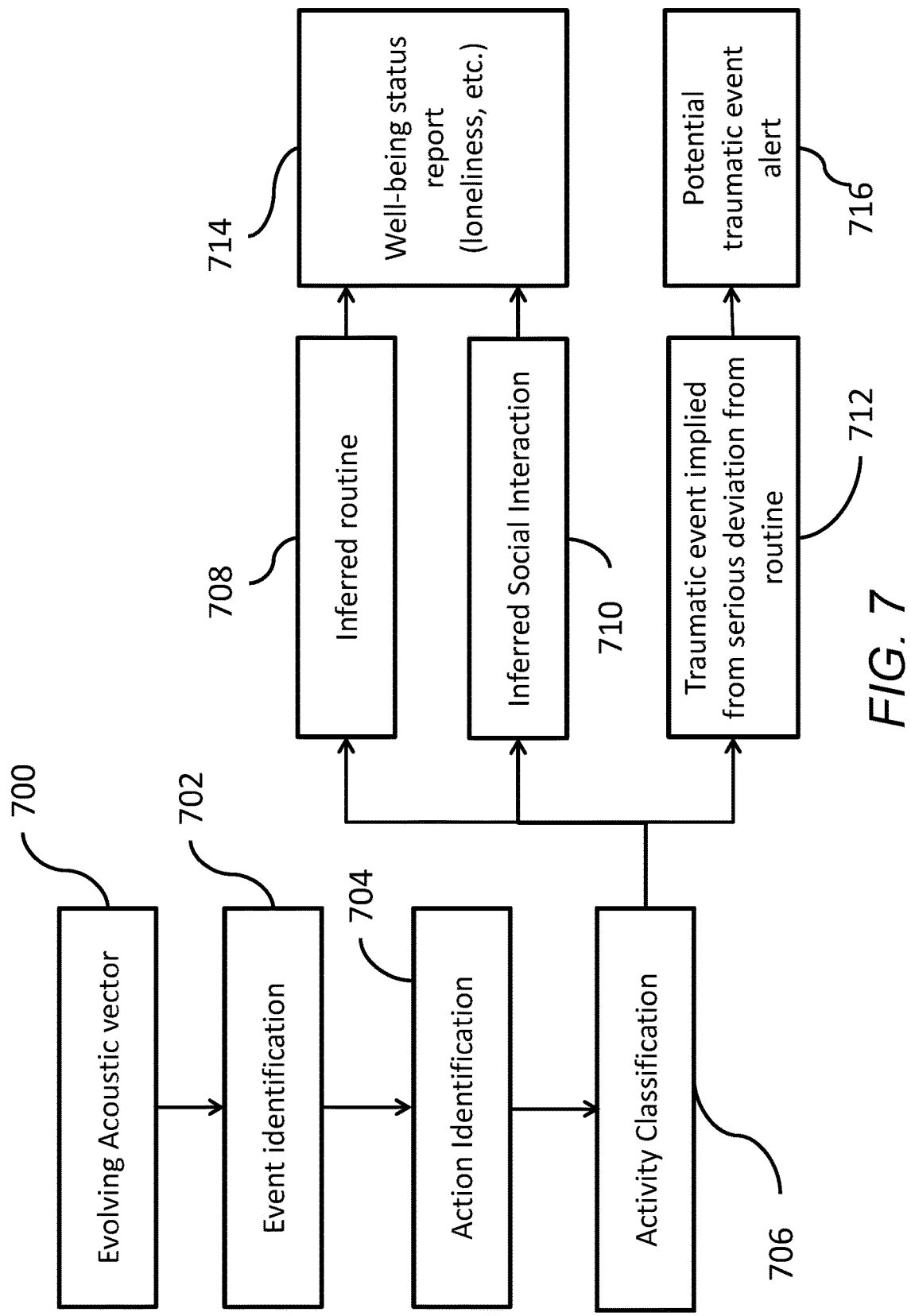
FIG. 7 shows an overview of a heuristic algorithm which processes acoustic vectors to identify events and actions, and to infer aspects of routine, social interaction and breaks in routine to provide a well-being status report and an alert for a potentially traumatic event.

FIG. 7 shows an overview of the heuristic algorithm which starts with an acoustic vector 700 (as discussed above) being scored for its similarity to an event type (event identification, 702). The potential event types and related scores are then fed into an action identifier 704 to assess what the most probable action is before the resulting series of probable actions are used to identify the most probable activity. The output of the activity classifier 706 allows daily routines to be inferred (708) along with social interaction and its associated parameters (710), which are used to form a well-being status report 714. This well-being status report can be used to measure loneliness and to check the stability and regularity of various activity routines. In addition, a break from a routine can also be inferred, at 712, which can provide an alert 716 indicating a potential traumatic event. The logic components that perform the inference of daily routines, social interactions and breaks in a routine may be referred to as an inference engine. A separate inference engine may be provided for each of the inferences 708, 710, 712, or a single inference engine may perform all of these types of inferences.

An action that has been identified as part of a routine can be formed from a series of identified and un-identified event signatures. To be identified as a routine action, the action has been observed a number of times; each time the likelihood of the constituent parts of the action is strengthened. For example the events involved in the action of making a cup of tea can include: filling a kettle, getting a cup out of the cupboard, opening the fridge and getting out milk, the kettle boiling, placing tea in the cup or tea pot, pouring water into the cup, or tea pot and so on. There are some events within the overall action that need to be completed in a certain order and there are certain events that are necessary for the action to be completed; in this case boiling kettles and pouring hot water. The likelihood that the action is completed is given by the combination of the linear progression of necessary ordered events and the presence (not necessarily in order, and possibly interleaved with the necessary ordered events) of the supplementary events. The events do not need categorical identification for them to affirm the action, just a pattern which is observed in a combined time-and-event space.

Returning to the example of an event set that makes up the action of "door-answering" we can see a heuristic technique where the action of going to the door and answering it comprises the events: walk_wood, walk_concrete, open_door. This would be a 'door answering' action. A set of actions that characterise a visit can be identified. Returning to the example, the 'door answering' action can be followed by conversation and a 'door closing' event. If 'door closing' is followed by 'conversation' it can be assumed that the visitor has entered the user's home. The length of the visit can be punctuated with a fresh 'door answering' action. The amount of conversation, how many speakers and the contribution from the user and others make to that conversation can be used as a measure of social interaction. Clearly, a 'door answering' action followed by 'door closing' and no subsequent acoustic activity inside the home implies the user has exited the building. Conversely a 'door opening' followed by 'door closing' and acoustic activity inside the home implies the user's return. It is possible for aspects of the acoustic signatures relating to the user to have been previously identified and stored, and so a likelihood score that the person entering the home is the user can be estimated. Once an acoustic signature has been identified which includes a generic conversation or voice event, aspects of that signature relating to the user can be gathered, so that the user's acoustic signatures can occupy a smaller volume of parameter space than that for the generic signature.

Other events, actions and processes present in daily life can be treated in a similar manner, such as the actions involved in making breakfast, having a drink, or making a cup of tea. This may be implemented both at a generic level and at a user identified level.

Series of actions that are recognisable and are not completed can indicate traumatic events. In such cases the set of actions has to be known to the control unit or acoustic monitoring device, either from machine learning or as a library file. Transitions of interest in the acoustic signature function are those from sounds associated with the user's normal actions to there being no sound originating within the user's home, or recognisable sound patterns equating to calls for help from the user. An example would be when the user gets up in the night and fails to return to bed. Another would be a fall, or collapse, where normal activity is interrupted. In place of the case where an acoustic signature for the 'fall' is being listened for, the device of the disclosure may also listen for normal activity turning into no activity, or for acoustic activity associated with someone weakly struggling. Such an event can be used to trigger an alert to an appropriate agency or person, which can either result in a telephone call or a visit.

Another case of use comes from the field of offender management where court orders for house arrest can include a requirement for no visitors or that only certain visitors are allowed. For example, the proposed device might be trained to alert the appropriate agencies if a female visitor is present in a sex offender's home.

In all cases the combination of the acoustic signatures for everyday events, actions and processes is analysed for content and context to provide a picture of interpersonal interactions, everyday routines and when traumatic events occur.

Various modifications and improvements can be made to the above without departing from the scope of the disclosure.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may comprise one or more modules that execute on one or more processors in a distributed, non-distributed, or multiprocessing environment.

The method as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

The invention claimed is:

1. An activity monitor for use in a building, the activity monitor comprising:
   one or more acoustic transducers; and
   a computation component that is arranged to identify events from acoustic signals received by the one or more acoustic transducers, wherein the computation component is configured:
      to sample a time slice of an incoming acoustic signal among the acoustic signals received by the one or more acoustic transducers;
      to derive a temporal characteristic from the sampled time slice;
      to generate a spectral characteristic of the time slice;
      to combine the temporal characteristic and the spectral characteristic of the time slice to form an acoustic vector; and
   wherein the computation component comprises a statistical model-based pattern recognition component arranged to analyse the acoustic vector to identify an event; and an event classifier configured to identify indoor actions formed from a sequence of different identified events, wherein a likelihood of an indoor action being performed is derived from a combination of a linear progression of events in a prescribed order; and the presence of supplementary events in any order.

2. The monitor of claim 1, wherein the identification of events is based on infra-sound acoustic signals or on acoustic signals of frequency less than 40 Hz, whereby intelligible speech is not captured.

3. The monitor of claim 1, further comprising an electronic filter circuit coupled with the one or more acoustic transducer that filters out frequency components of the acoustic signal which relate to intelligible speech.

4. The monitor of claim 1, wherein the computation component is configured to map the acoustic vector to a multidimensional space comprising axes which correspond to age and sex characteristics.

5. The monitor of claim 1, wherein the computation component further comprises at least one of a local data store comprising a library of pre-stored or learned events; and
   an activity classifier that identifies activities formed from sequences of actions.

6. The monitor of claim 5, wherein the computation component is arranged such that, if an acoustic vector is not matched to an event by the local data store, the computation component sends the acoustic vector to a server which comprises a library of events and which compares the acoustic vector with the library; and if a match is found, the server sends information back to the computation component which then updates the local data store of the computation component.

7. The monitor of claim 1, wherein the computation component further comprises an inference engine that infers at least one of:
   a routine from identified actions or activities;
   a social interaction from identified actions or activities; and
   a sudden break in routine from identified actions or activities, to indicate a possible traumatic event.

8. The monitor of claim 1, wherein the computation component is configured to monitor movement of a person.

9. The monitor of claim 8, being arranged to identify movement in specific rooms and/or use of specific doors within the building.

10. The monitor of claim 1, being arranged to learn the voice of a user and identify additional voices.

11. The monitor of claim 1, being arranged to measure (i) the duration of a visit of a person visiting another person present in the building, by recording time periods of different voices or the time between doors of the building being opened or closed and, time periods of a second set of footsteps different from a first set of footsteps of the person present in the building and/or (ii) the proportion of conversation spoken by each participant in the conversation.

12. The monitor of claim 1, wherein a visitor is visiting another person present in the building, the monitor being arranged to:
   (i) monitor a level of animation, a tone of voice; and/or
   (ii) store voices and identify regular visitors and monitor timing and duration of their visits.

13. The monitor of claim 1, wherein a visitor is visiting another person present in the building, the monitor being arranged to rank voices either on male-female scale or on age-related scale, giving scores to voices.

14. The monitor of claim 1, wherein the one or more acoustic transducers form part of an acoustic monitoring unit and wherein the activity monitor further comprises a plurality of acoustic monitoring units.

15. The monitor of claim 14, wherein the acoustic monitoring units are provided in a plurality of rooms or areas of the building, or a plurality of areas of the outdoor space.

16. The monitor of claim 14, wherein each of the acoustic monitoring units comprises an acoustic transmitter, each acoustic monitoring unit being arranged to receive outputs of one or more acoustic transmitters; the monitor being adapted to determine relative positions between two or more acoustic monitoring units using the outputs of the one or more acoustic transmitters and thus to triangulate the position of a detected sound.

17. A method of monitoring activity, comprising obtaining acoustic signals and computationally identifying events from the acoustic signals by:
   sampling a time slice of an acoustic signal among the acoustic signals;
   deriving a temporal characteristic from the sampled time slice;
   generating a spectral characteristic of the time slice;
   combining the temporal characteristic and the spectral characteristic of the time slice to form an acoustic vector; and
   analysing the acoustic vector for identification of an event using a statistical pattern recognition model
   providing an event classifier configured to identify indoor actions formed from a sequence of different identified events, and
   identifying indoor actions wherein a likelihood of an indoor action being performed is derived from a combination of a linear progression of events in a prescribed order; and the presence of supplementary events in any order.

18. A non-transitory computer readable medium having stored thereon instructions that, when executed by a computer, enable the computer it to:
- sample a time slice of an acoustic signal received by an acoustic transducer;
- derive a temporal characteristic from the sampled time slice;
- generate a spectral characteristic of the time slice;
- combine the temporal characteristic and the spectral characteristic of the time slice to form an acoustic vector; and
- analyse the acoustic vector for identification of an event using a statistical pattern recognition model
- identify indoor actions formed from a sequence of different identified events using an event classifier, wherein a likelihood of an indoor action being performed is derived from a combination of a linear progression of events in a prescribed order; and the presence of supplementary events in any order.

* * * * *